United States Patent [19]

Lloyd

[11] Patent Number: 5,153,347
[45] Date of Patent: Oct. 6, 1992

[54] PHOSPHONATE, PHOSPHINATE DERIVATIVES USEFUL AS ANTIHYPERTENSIVE AGENTS

[75] Inventor: John E. Lloyd, Yardley, Pa.

[73] Assignee: E. R. Squibb & Sons, Inc., Princeton, N.J.

[21] Appl. No.: 648,245

[22] Filed: Jan. 31, 1991

[51] Int. Cl.$^5$ .......................... C07F 9/32; C07F 9/40; C07F 9/53

[52] U.S. Cl. .................... 558/179; 548/119; 549/218; 558/180; 558/182; 558/188; 558/189; 558/190; 558/192; 558/193; 558/196; 558/197; 558/198; 568/15

[58] Field of Search .............. 548/119; 558/179, 189, 558/198; 568/15

[56] References Cited

U.S. PATENT DOCUMENTS

| | | | |
|---|---|---|---|
| 4,207,324 | 6/1980 | Mastsumura et al. | 514/397 |
| 4,340,598 | 7/1982 | Furukawa et al. | 514/400 |
| 4,355,040 | 10/1982 | Furukawa et al. | 514/400 |
| 4,582,847 | 4/1986 | Furukawa et al. | 514/400 |
| 4,812,462 | 3/1989 | Blankley et al. | 514/303 |
| 4,816,463 | 3/1989 | Blankley et al. | 514/293 |
| 4,820,843 | 4/1989 | Aldrich et al. | 548/252 |
| 4,870,186 | 9/1989 | Aldrich et al. | 548/215 |
| 4,874,867 | 10/1989 | Aldrich et al. | 548/101 |
| 4,880,804 | 11/1989 | Carini et al. | 514/234.5 |

FOREIGN PATENT DOCUMENTS

| | | |
|---|---|---|
| 253320 | 1/1988 | European Pat. Off. |
| 323841 | 7/1989 | European Pat. Off. |
| 324377 | 7/1989 | European Pat. Off. |

Primary Examiner—Mary C. Lee
Assistant Examiner—Michael G. Ambrose
Attorney, Agent, or Firm—Theodore R. Furman, Jr.

[57] ABSTRACT

Novel angiotensin II receptor antagonists of the formula

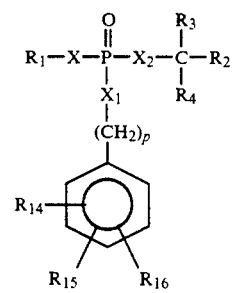

wherein X, $X_1$, $X_2$, $R_1$, $R_2$, $R_3$, $R_4$ and $R_5$ are as defined herein, are disclosed. These compounds are useful, for example, in the treatment of hypertension, congestive heart failure and cardiac hypertrophy.

5 Claims, No Drawings

PHOSPHONATE, PHOSPHINATE DERIVATIVES USEFUL AS ANTIHYPERTENSIVE AGENTS

FIELD OF THE INVENTION

The present invention relates to novel substituted phosphorus containing compounds which are useful as antihypertensive agents.

SUMMARY OF THE INVENTION

In accordance with the present invention, novel compounds which inhibit the action of the hormone angiotensin II are disclosed. These compounds are of the general formula

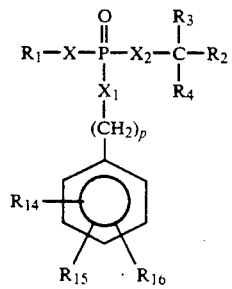

and pharmaceutically acceptable salts thereof;

wherein X, $X_1$ and $X_2$ are each independently —NH—, —O—, —S—, —$CH_2$— or a single bond;

R is alkyl of 2 to 10 carbon atoms, alkenyl or alkynyl of 3 to 10 carbon atoms or the same groups substituted with F or $CO_2R_{15}$; cycloalkyl of to 8 carbon atoms, cycloalkylalkyl, of 4 to 10 carbon atoms; cycloalkylalkenyl or cycloalkylalkynyl of 5 to 10 carbon atoms; $(CH_2)_sZ(CH_2)_mR'$ (wherein R' is H, $C_{1-6}$alkyl, $C_{3-6}$cycloalkyl, $C_{2-4}$alkenyl or $C_{2-4}$alkynyl) optionally substituted with F or $CO_2R_{15}$; benzyl or benzyl substituted on the phenyl ring with 1 or 2 halogens, alkyl of 1 to 4 carbon atoms or nitro;

$R_2$ is H, CN, $COOR_6$, alkyl of 1 to 10 carbon atoms, alkenyl of 3 to 10 carbon atoms, or the same groups substituted with F; phenylalkenyl wherein the aliphatic portion is 2 to 6 carbon atoms; —$(CH_2)_m$-imidazol-1-yl; —$(CH_2)_m$-1,2,3-triazolyl optionally substituted with one or two groups selected from $CO_2CH_3$ or alkyl of 1 to 4 carbon atoms;

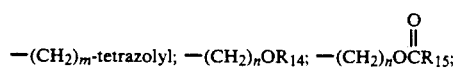

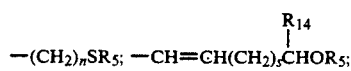

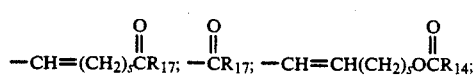

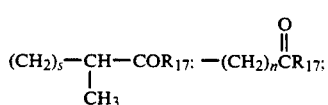

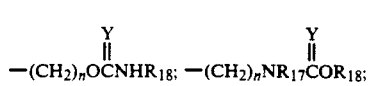

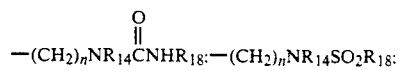

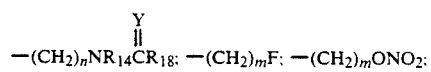

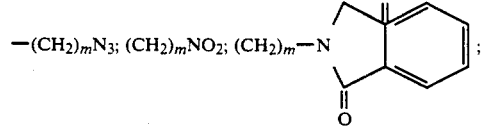

$R_3$ and $R_4$ are each independently hydrogen, alkyl, aryl or arylalkyl;

$R_5$ is hydrogen or alkyl of 1 to 4 carbons;

$R_6$ is H, alkyl or perfluoroalkyl of 1 to 8 carbon atoms, cycloalkyl of 3 to 6 carbon atoms, phenyl or benzyl;

$R_7$ is H, alkyl of 1 to 6 carbon atoms, cycloalkyl of 3 to 6 carbon atoms, phenyl, benzyl, acyl of 1 to 4 carbon atoms, phenacyl;

$R_8$ is H, alkyl of 1 to 6 carbon atoms, cycloalkyl of 3 to 6 carbon atoms, $(CH_2)_pC_eH_5$, $OR_{10}$ or $NR_{11}R_{12}$;

$R_9$ is alkyl of 1 to 6 carbon atoms or perfluoroalkyl of 1 to 6 carbon atoms, 1-adamantyl, 1-naphthyl, 1-(1-naphthyl)ethyl, or $(CH_2)_pC_6H_5$;

$R_{10}$ is H, alkyl of 1 to 6 carbon atoms, cycloalkyl of 3 to 6 carbon atoms, phenyl or benzyl;

$R_{11}$ and $R_{12}$ independently are H, alkyl of 1 to 4 carbon atoms, phenyl, benzyl, α-methylbenzyl, or taken together form a ring of the formula

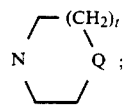

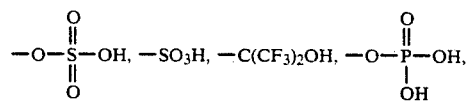

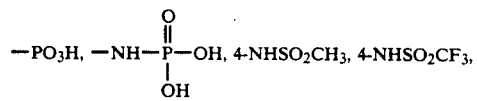

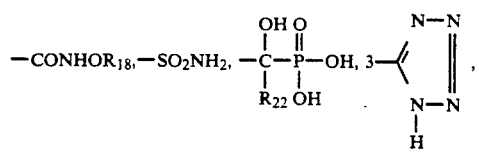

-continued

[Structures shown: 4-X₃-tetrafluorophenyl with R₂₃ and NC=O/HOC=O group; 4X₃-naphthyl with R₂₃; biphenyl with X₃ and R₂₃;

4-CONH—(tetrazole), 4-CONHNHSO₂CF₃,

4-CONH—CH(CO₂H)CH₂C₆H₅, 4-CO—N(pyrrolidine-CO₂H),

HO₂C / R₂₇ / Z / R₂₇ substituted ring, 4-(triazole-CF₃ with NH), 4-(triazole with R₂₆, NH), 4-X-cyclohexyl with R₂₃, 4-N-phthalimide with R₇, R₈, R₂₃, —C(=O)—NHSO₂—(CH₂)ₛ-phenyl-R₂₈ ]

R₁₅ is H, halogen, —NO₂, —CN, alkyl of 1 to 4 carbons, acyloxy of 1 to 4 carbons, alkoxy of 1 to 4 carbons, —CO₂H, CO₂R₁₇, —NHSO₂CH₃, —NHSO₂CF₃, —CONHOR₁₈, —SO₂NH₂, aryl, furyl or

[tetrazole structure];

R₁₆ is H, halogen, alkyl of 1 to 4 carbons or alkoxy of 1 to 4 carbons;

R₁₇ is hydrogen or $$-\underset{R_{18}}{\overset{|}{C}}H-OCR_{19};$$

R₁₈ is hydrogen, methyl or benzyl;

R¹⁹ is alkyl of 1 to 6 carbons, NR₂₀R₂₁;

R₂₀ and R₂₁ are independently hydrogen, benzyl, alkyl of 1 to 6 carbons or taken together are 3 to 6 methylene groups forming a 4- to 7-membered ring with the nitrogen atom to which they are attached;

R₂₂ is hydrogen, alkyl of 1 to 5 carbons or phenyl;

R₂₃ is —CO₂H, —CO₂R₁₇, —CH₂CO₂H, —CH₂CO₂R₁₇,

—O—S(O)(OH)—OH, —O—P(O)(OH)—OH, —SO₃H, —NHP(O)(OH)—OH,

—PO₃H, —C(CF₃)₂OH, —NHSO₂CH₃, —NHSO₂CF₃,

—NHCOCF₃, —CONHOR₁₈, —SO₂NH₂, —C(R₂₂)(OH)—P(O)(OH)—OH,

[tetrazole]—CH₂, [tetrazole], —CONH—[tetrazole],

—CONHNHSO₂CF₃, [triazole-CF₃] or

[pyrazole with R₂₆];

R₂₄ is H, alkyl of 1 to 4 carbons, —CH₂CH=CH₂ or —CH₂C₆H₄R₂₅;

R₂₅ is H, —NO₂, —NH₂, —OH or —OCH₃;

R₂₆ is —CN, —NO₂ or —CO₂R₂₇;

R₂₇ is H, alkyl of 1 to 6 carbons, cycloalkyl of 3 to 6 carbons, phenyl or benzyl;

R₂₈ and R₂₈' are independently H, alkyl of 1 to 5 carbons or phenyl;

X₃ is a carbon-carbon single bond —CO—, —CH₂—, —O—, —S—, —NH—,

—N(R₂₉)—, —CON(R₂₁)—, —NCO(R₂₁)—,

—OCH₂—, —CH₂O, —SCH₂—, —CH₂—S—, —NHC(R₂₈)(R₂₈')—, —NR₂₁SO₂—, —SO₂NR₂₁, —C(R₂₈)(R₂₈')NH, —CH=CH—, —CF=CF—, —CH=CF—, —CF=CH—, —CH₂CH₂—, —CF₂CF₂—,

—CH(OR₃₀)—, —CH(OCOR₂₇)—, —C(=NR₃₁)— or —C(OR₃₂)(OR₃₃)—;

R₂₉ is H, alkyl of 1 to 6 carbons, benzyl or alkyl;

R₃₀ is H, alkyl or perfluoroalkyl of 1 to 8 carbons, cycloalkyl of 3 to 6 carbons, phenyl or benzyl;

R₃₁ is —N(R₂₈)(R₂₈')—NHCONH₂, —NHCSNH₂,

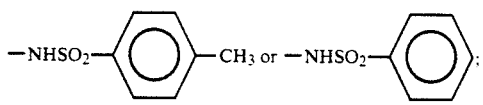 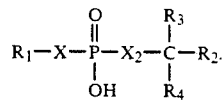

$R_{32}$ and $R_{33}$ are independently alkyl of 1 to 4 carbons or taken together are —(CH$_2$)q;
Y=O or S;
Z=O, NR$_9$ or S;
m is 1–5;
n is 1–10;
p is 0–3;
q is 2–3;
r is 0–2;
s is 0–5;
t is 0 or 1; and
x is 1 to 6.

DETAILED DESCRIPTION OF THE INVENTION

In its broadest aspects the present invention relates to the compounds of formula I and to pharmaceutical compositions and methods employing such compounds.

The term "aryl", as used throughout the specification either by itself or as part of a larger group, refers to phenyl or phenyl substituted with halogen, alkyl, alkoxy, alkylthio, hydroxy, alkanoyl, nitro, amino, dialkylamini, or trifluoromethyl groups. Phenyl and monosubstituted phenyl are preferred and phenyl is the most preferred.

The term "alkyl", as used throughout the specification either by itself or as part of a larger group, refers to groups having 1 to 10 carbon atoms. Alkyl groups having 1 to 4 carbon atoms are preferred.

The term "cycloalkyl", as used throughout the specification either by itself or as part of a larger group, refers to groups having 3 to 7 carbon atoms.

The term "alkoxy", as used throughout the specification either by itself or as part of a larger group, refers to groups having 1 to 8 carbon atoms. Alkoxy groups having 1 to 3 carbon atoms are preferred.

The term "halogen", as used by itself or as part of a larger group refers to fluorine, chlorine, bromine and iodine with fluorine and chlorine being preferred.

To prepare the compounds of formula I wherein X is —O— and X$_2$ is CH$_2$ or a single bond, a compound of the formula

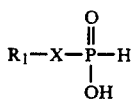   II is treated with a silylating agent, such as trimethylsilyl chloride, and a base, such as triethylamine, and thereafter coupled with a compound of the formula

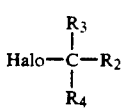   III to provide the intermediate of the formula

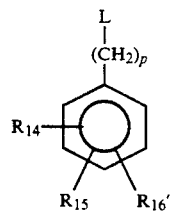   IV

Compound IV, in a solvent such as acetonitrile, and in the presence of a base, such as diazobicycloundecene is reacted with a compound of the formula

   V wherein L is a leaving group, e.g., halo, mesyl or tosyl, and thereafter deprotected using known methodology to provide the compounds of formula I.

Compounds of formula V can be prepared as described in EP 0 253 310 to DuPont.

Compounds of formula II are readily prepared by known methodology, e.g., by combining $R_1XH$   VI where X is a single bond and $R_1$ is alkenyl with sodium hypophosphite in an inert solvent such as acetonitrile with a radical initiator, such as azobisisobutyrylnitrile.

To prepare compounds of formula I where X$_2$ is —O—, compounds of formula II, in a solvent such as acetonitrile or tetrahydrofuran can be reacted with a compound of the formula

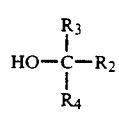   VII in the presence of a coupling agent, such as dicyclohexylcarbodiimide to provide intermediates of the formula

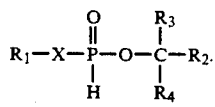   VIII

Intermediates of formula VIII can thereafter be treated with an oxidizing agent, such as sodium periodate, to provide intermediates of formula IV where X$_2$ is —O—. These can be reacted with compounds of formula V as above to provide the corresponding products.

To prepare compounds of formula I where X$_1$ is —NH— and X$_2$ is —O—, an intermediate of formula VIII in a solvent such as carbon tetrachloride can be treated with chlorine and thereafter reacted with a compound of the formula

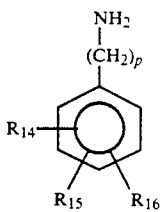

in a solvent, such as tetrahydrofuran, and in the presence of an organic base, such as triethylamine.

To prepare compounds of formula I wherein $X_1$ is a single bond and $X_2$ is —O—, a compound of formula II is reacted with a compound of formula V to provide the intermediate

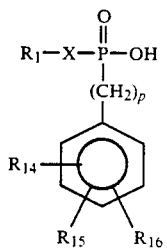

under conditions as described above for the reaction of intermediates II and III. Thereafter, a compound of formula III can be reacted with intermediate X under conditions as described above for compounds IV and V to provide the products of formula I wherein X' is a single bond and $X_2$ is —O—.

Preferred compounds in accordance with the present invention are those wherein

X is —$CH_2$— or a single bond;
$X_1$ is —O—, —NH— or a single bond;
$X_2$ is —O—, —$CH_2$— or a single bond;
$R_1$ is alkyl;
$R_2$ is $COOR_6$;
$R_3$ is H;
$R_4$ is H; and,
$R_{14}$ is r—$X_3$

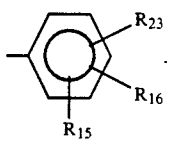

Most preferred compounds in accordance with the present invention are those wherein X is —$CH_2$—;
$X_1$ is —O—;
$X_2$ is a single bond;
$R_1$ is n-butyl;
$R_2$ is $COOCH_3$;
$R_3$ is H;
$R_4$ is H;
$R_{14}$ is a

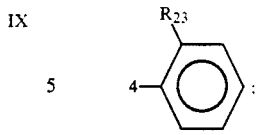

and $R_{23}$ is —COOH or tetrazolyl.

The present compounds of formula I inhibit the action of the hormone angiotensin II (A-II) and are therefore useful, for example, as antihypertensive agents.

The action of the enzyme renin on angiotensinogen, a pseudoglobulin in blood plasma, produces angiotensin I. Angiotensin I is converted by angiotensin converting enzyme (ACE) to angiotensin II. The latter is an active pressor substance which has been implicated as the causative agent in several forms of hypertension in various mammalian species, e.g., humans. The compounds of this invention inhibit the action of A-II at its receptors on target cells and thus prevent the increase in blood pressure produced by this hormonereceptor interaction. Thus by the administration of a composition containing one (or a combination) of the compounds of this invention, angiotensin dependent hypertension in a species of mammal (e.g., humans) suffering therefrom is alleviated. A single dose, or preferably two to four divided daily doses, provided on a basis of about 0.1 to 100 mg per kilogram of body weight per day, preferably about 1 to 15 mg per kilogram of body weight per day is appropriate to reduce blood pressure. The substance is preferably administered orally, but intranasal, transdermal and parenteral routes such as the subcutaneous, intramuscular, intravenous or intraperitoneal routes can also be employed. The compounds of this invention are also useful in the treatment of congestive heart failure and cardiac hypertrophy.

The compounds of this invention can also be formulated in combination with a diuretic for the treatment of hypertension. A combination product comprising a compound of this invention and a diuretic can be administered in an effective amount which comprises a total daily dosage of about 30 to 600 mg, preferably about 30 to 330 mg of a compound of this invention, and about 15 to 300 mg, preferably about 15 to 200 mg of the diuretic, to a mammalian species in need thereof. Exemplary of the diuretics contemplated for use in combination with a peptide of this invention are the thiazide diuretics, e.g., chlorthiazide, hydrochlorthiazide, flumethiazide, hydroflumethiazide, bendroflumethiazide, methylchlothiazide, trichlormethiazide, polythiazide or benzthiazide as well as ethacrynic acid, ticrynafen, chlorthalidone, furosemide, musolimine, bumetanide, triamterene, amiloride and spironolactone and salts of such compounds.

The compounds of formula I can be formulated for use in the reduction of blood pressure in compositions such as tablets, capsules or elixirs for oral administration, in sterile solutions or suspensions for parenteral or intranasal administration, or in transdermal patches. About 10 to 500 mg of a compound of formula I is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The present invention can be further illustrated by the following examples.

EXAMPLE 1

4'-[[[(2-Methoxy-2-oxoethyl)pentylphosphinyl]oxy]methyl][1,1'-biphenyl]-2-carobyxlic acid A. Pentylphosphinic acid To a stirred suspension of sodium hypophosphite (56 g) in 500 ml of absolute ethanol was added concentrated sulfuric acid (14 ml), then 1-pentene (11.9 g, 0.17 mole), and azobixisobutyronitrile (2.7 g). The reaction flask was equipped with a dry ice condenser, and the reaction mixture was heated to reflux overnight. The cooled mixture was filtered through sintered glass, and the filtrate was concentrated in vacuo. The clear oil was dissolved in water (160 ml), made basic with 50% sodium hydroxide (pH 13) and washed with ether (2×100 ml). The aqueous solution was acidified with concentrated sulfuric acid (pH 1.5) and product was extracted with ethyl acetate (300 ml). The organic phase was washed with brine, dried over anhydrous magnesium sulfate and concentrated in vacuo to active 21.7 g of the title A pentylphosphonous acid as a clear, colorless oil.

B. (Hydroxypentylphosphinyl)acetic acid, methyl ester

The title A phosphonous acid (2.0 g, 14.7 mmol) was dissolved in chloroform (40 mL) at room temperature under argon. Triethylamine (4.7 mL, 32.4 mmol) was added and the resulting mixture was cooled to 0°. Trimethylsilyl chloride (4.1 mL, 29.4 mmol) was added and the mixture was stirred for 30 minutes. Methyl bromoacetate (0.42 g, 1.2 mmol) was added and the resulting mixture was stirred for 5 hours. The volatiles were evaporated and the residue was partitioned with ethyl acetate and saturated aqueous sodium bicarbonate. The pH of the aqueous layer was adjusted to 2 with hydrochloric acid. The aqueous phase was extracted with ethyl acetate and the combined organic extracts were washed with brine, dried over magnesium sulfate, filtered and the solvents removed to yield 2.08 g of the title B compound as a light yellow oil.

C. 4'-[[(2-Methoxy-2-oxoethyl)pentylphosphinyl]-oxymethyl][1,1-biphenyl]-2-carboxylic acid, 1,1-dimethylethyl ester The title B phosphinic acid (340 mg, 1.63 mmol) was dissolved in acetonitrile (15 mL) at room temperature under nitrogen. 1,8-Diazabicyclo[5.4.0]undec-7-ene (0.27 mL, 1.80 mmol) and 4'-(bromomethyl)[1,1'-biphenyl]-2-carboxylic acid, 1,1-dimethylethyl ester (630 mg, 1.80 mmol) (prepared as described in European Patent Application 0 253 310 to DuPont) were added and the resulting mixture was stirred for 18 hours. The volatiles were evaporated and the residue was partitioned between ethyl acetate and 1N hydrochloric acid. The organic extracts were washed with saturated aqueous sodium bicarbonate and brine, dried over magnesium sulfate, filtered and the solvent evaporated to yield 637 mg of a crude residue as a yellow oil. Purification of this residue by flash chromatography yielded 266 mg of the title C compound as a yellow oil.

D. 4'-[[[(2-Methoxy-2-oxoethyl)pentylphosphinyl]-oxy]methyl][1,1'-biphenyl]-2-carboxylic acid The title C phosphinate (156 mg, 0.33 mmol) was dissolved in methylene chloride (4 mL) and cooled to 0°. Following the addition of anisole (1.6 mL), trifluoroacetic acid (4 mL) was added and the resulting mixture was stirred for 45 minutes. Toluene (-50 mL) was added and the volatiles were removed. The residue was partitioned between ethyl acetate and saturated aqueous sodium bicarbonate. The aqueous layer was acidified to pH 2 by the addition of concentrated hydrochloric acid, extracted with ethyl acetate, and the combined organic layers were dried over anhydrous magnesium sulfate, filtered, and the volatiles removed. The residue was purified by preparative high pressure liquid chromatography to yield 36 mg of the title compound as a white powder, m.p. 101°–102°.

EXAMPLE 2

4'-[[[(2-Methoxyethoxy)pentylphosphinyl]oxymethyl[1,1'-biphenyl-2-carboxylic acid, monosodium salt A. Pentylphosphonic acid, mono(2-methoxyethyl)ester The title A compound of Example 1 (1.1 g, 8.0 mmol) and 2-methoxyethanol (1.3 mL, 16.0 mmol) were dissolved in tetrahydrofuran (30 mL) at room temperature under argon. 1,3-Dicyclohexylcarbodiimide (2.2 g, 10.4 mmol) and 4-dimethylaminopyridine (251 mg) were added and the resulting mixture was stirred for 2 hours. The mixture was filtered to remove the dicyclohexylurea, the precipitate was washed well with ethyl acetate, and the organics were washed with 5aqueous potassium bisulfate, saturated aqueous sodium bicarbonate and brine. The organic layer was dried over magnesium sulfate and filtered. The volatiles were evaporated and the residue was dissolved in p-dioxane (31 mL). A solution of sodium periodate (2.1 g, 9.6 mmol) in water (19 mL) was added and the resulting mixture was stirred for 18 hours. The mixture was partitioned between ethyl acetate and 5% aqueous potassium bisulfate and the aqueous layer was extracted with ethyl acetate. The combined organic layers were washed with brine, dried over magnesium sulfate and filtered. The volatiles were evaporated to yield 213 mg of the title A compound as a yellow oil.

B. 4'-[[[(2-Methoxyethoxy)pentylphosphinyl]-oxy]methyl[1,1'-biphenyl]-2-carboxylic acid, 1,1-dimethylethyl ester The title A phosphonic acid (130 mg, 0.62 mmol) was dissolved in acetonitrile (6 mL) at room temperature under nitrogen. 1,8-Diazabicyclo[5.4.0]undec-7-ene (0.11 mL, 0.68 mmol) and 0 4'-(bromomethyl)[1,1'-biphenyl-2-carboxylic acid, 1,1-dimethylethyl ester (238 mg, 0.68 mmol) were added and the resulting mixture was stirred for 72 hours. The volatiles were evaporated and the residue was partitioned between ethyl acetate and 1N hydrochloric acid. The organic extracts were washed with saturated aqueous sodium bicarbonate and brine, dried over magnesium sulfate, filtered and the solvent evaporated to yield 236 mg of a crude residue as a yellow oil. Purification of this residue by flash chromatography yielded 179 mg of the title B compound as a yellow oil. C. 4'-[[[(2-Methoxyethoxy)pentylphosphinyl]-oxymethyl][1,1'-biphenyl]-2-carboxylic acid, monosodium salt The title B compound (149 mg, 0.31 mmol) was dissolved in methylene chloride (4 mL) and cooled to 0°. Following the addition of anisole (1.6 mL), trifluoroacetic acid (4 mL) was added and the resulting mixture was stirred for 2.25 hours. Toluene (50 mL) was added and the volatiles were removed. The residue was partitioned between ethyl acetate and saturated aqueous sodium bicarbonate. The aqueous layer was acidified to pH 2 by the addition of concentrated hydrochloric acid, extracted with ethyl acetate, and the combined organic layers were dried over magnesium sulfate, filtered, and the volatiles removed. The residue was purified by preparative high pressure liquid chromatography to yield 44 mg of the title compound as a white powder, m.p. 101°–102°.

What is claimed is:

1. A compound of the formula

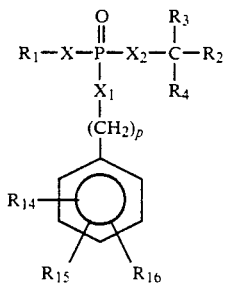

or pharmaceutically acceptable salts thereof;
wherein X is —CH$_2$— or a single bond; X$_1$ is —O— or a single bond; X$_2$ is —Ch$_2$—, —O— or a single bond;
R$_1$ is alkyl of 2 to 10 carbon atoms, alkenyl or alkynyl of 3 to 10 carbon atoms or the same groups substituted with F;
R$_2$ is H, COOR$_6$, alkyl of 1 to 10 carbon atoms, alkenyl of 3 to 10 carbon atoms, or the same groups substituted with F;
R$_3$ and R$_4$ are each independently hydrogen, alkyl, aryl or arylalkyl;
R$_6$ is alkyl or perfluoroalkyl of 1 to 8 carbon atoms, cycloalkyl of 3 to 6 carbon atoms, phenyl or benzyl; R$_{14}$ is

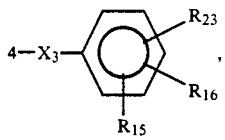

R$_{15}$ is H, halogen, —NO$_2$, —CN, alkyl of 1 to 4 carbons, acyloxy of 1 to 4 carbons, alkoxy of 1 to 4 carbons, —CO$_2$H, CO$_2$R$_{17}$, —NHSO$_2$CH$_3$, —NHSO$_2$CF$_3$, —CONHOR$_{18}$, —SO$_2$NH$_2$, aryl, furyl or

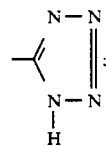

R$_{16}$ is H, halogen, alkyl of 1 to 4 carbons or alkoxy of 1 to 4 carbons;
R$_{17}$ is hydrogen or

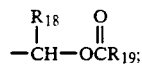

R$_{18}$ is hydrogen, methyl or benzyl;
R$_{19}$ is alkyl of 1 to 6 carbons, NR$_2$R$_{21}$;
R$_{20}$ and R$_{21}$ are independently hydrogen, benzyl, alkyl of 1 to 6 carbons or taken together are 3 to 6 methylene groups forming a 4- to 7-membered ring with the nitrogen atom to which they are attached;
R$_{23}$ is —CO$_2$H, —CO$_2$R$_{17}$,
X$_3$ is a carbon-carbon single bond, —CO—, —CH$_2$—, and 2. A compound of claim 1 wherein
X is —CH$_2$— or a single bond;
X is —O—, or a single bond;
X$_2$ is —O—, —CH$_2$— or a single bond;
R$_1$ is alkyl;
R$_2$ is COOR$_6$;
R$_3$ is H;
R$_4$ is H; and,
R$_{14}$ is

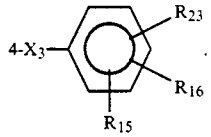

3. A compound of claim 1 wherein
X is —CH$_2$—;
X$_1$ is —O—;
X$_2$ is a single bond;
R$_1$ is n-butyl;
R$_2$ is COOCH$_3$;
R$_3$ is H;
R$_4$ is H;
R$_{14}$ is

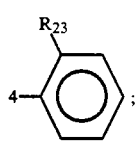

and
R$_{23}$ is —COOH

4. A compound of claim 1 having the name 4'-[[[(2-methoxy-2-oxoethyl)pentylphosphinyl]oxy]methyl][1,1'-biphenyl]-2-carboxylic acid.

5. A compound having the name 4'-[[[(2-methoxyethoxy)pentylphosphinyl]oxy]-methyl][1,1'-biphenyl]-2-carboxylic acid, monosodium salt.

* * * * *